United States Patent
Adcock

(10) Patent No.: US 7,727,528 B2
(45) Date of Patent: Jun. 1, 2010

(54) METHODS FOR DIAGNOSIS USING ANTI-CYTOKINE RECEPTOR ANTIBODIES

(75) Inventor: Deborah Kay Adcock, Shreveport, LA (US)

(73) Assignee: Early Detection, LLC, Shreveport, LA (US)

( * ) Notice: Subject to any disclaimer, the term of this patent is extended or adjusted under 35 U.S.C. 154(b) by 761 days.

(21) Appl. No.: 11/185,335

(22) Filed: Jul. 20, 2005

(65) Prior Publication Data

US 2006/0039857 A1 Feb. 23, 2006

Related U.S. Application Data

(60) Provisional application No. 60/590,400, filed on Jul. 22, 2004.

(51) Int. Cl.
| | |
|---|---|
| A61K 39/395 | (2006.01) |
| A61K 39/00 | (2006.01) |
| A61K 31/00 | (2006.01) |
| A61K 38/00 | (2006.01) |
| G01N 23/00 | (2006.01) |
| G01N 33/48 | (2006.01) |
| G01N 21/00 | (2006.01) |
| G01N 21/75 | (2006.01) |
| A01N 61/00 | (2006.01) |
| A01N 37/18 | (2006.01) |

(52) U.S. Cl. ............. 424/143.1; 424/130.1; 424/133.1; 424/138.1; 436/57; 436/64; 436/164; 514/1; 514/2

(58) Field of Classification Search .............. 424/130.1, 424/133.1, 138.1, 143.1; 436/57, 64, 164; 514/1, 2

See application file for complete search history.

(56) References Cited

U.S. PATENT DOCUMENTS

| | | | |
|---|---|---|---|
| 2002/0012665 A1 | 1/2002 | Hanna | |
| 2002/0146369 A1 | 10/2002 | Goldenberg | |
| 2003/0054421 A1 | 3/2003 | Rosen et al. | |
| 2003/0138426 A1* | 7/2003 | Ni et al. | 424/146.1 |
| 2003/0185832 A1 | 10/2003 | Thorpe et al. | |
| 2005/0089928 A1* | 4/2005 | Short et al. | 435/7.1 |

FOREIGN PATENT DOCUMENTS

| | | |
|---|---|---|
| WO | WO 94/02627 | 2/1994 |
| WO | WO 03/056896 | 7/2003 |
| WO | WO 2005/107802 A2 * | 11/2005 |

OTHER PUBLICATIONS

Lavabre-Bertrand, Thierry. Detection of membrane and soluble interleukin-6 receptor in lymphoid malignancies British Journal of Haematology 91(4): 871-877, Dec. 1995.*
Qui, Yuhua et al. Establishment and application of radioimmunoassay for detecting human soluble IL-6Ralpha. Zhonghua Jianyan Yixue Zazhi 26(7): 424-427, 2003.*
Abbate, et al., "Tumor necrosis factor and soluble interleukin-2 receptor: two immunological biomarkers in female neoplasms", *Eur J Gynaecol Oncol*, 13(1 Suppl):92-6 (1992).
Adair, "Engineering antibodies for therapy", *Immunol. Rev.*, 130:5-40 (1992).
Aggarwal, et al., "The role of TNF and its family members in inflammation and cancer: lessons from gene deletion", *Curr Drug Targets Inflamm Allergy*, 1(4):327-41 (2002).
Ardizzoia, et al., "Tumor necrosis factor in solid tumors: increased blood levels in the metastatic disease", *J Biol Regul Homeost Agents*, 6(3):103-7 (1992).
Berkower, "The promise and pitfalls of monoclonal antibody therapeutics", *Curr. Opin. Biotechnology*, 7:622-8 (1996).
Bjornberg, et al., "Mechanisms involved in the processing of the p55 and the p75 tumor necrosis factor (TNF) receptors to soluble receptor forms", *Lymphokine Cytokine Res.*, 13(3):203-11 (1994).
Bouwmeester, et al., "A physical and functional map of the human TNF-alpha/NF-kappa B signal transduction pathway", *Nat Cell Biol*, 6(2):97-105 (2004).
Brumley, et al., "Radiolabeled monoclonal antibodies", *AORN J.*, 62: 343-355 (1995).
Clackson, et al., "Making antibody fragments using phage display libraries", *Nature*, 352(6336):624-688 (1991).
Csehi, et al., "Tumor necrosis factor (TNF) interferes with insulin signaling through the p55 TNF receptor death domain", *Biochem Biophys Res Commun*, 329(1):397-405 (2005).

(Continued)

*Primary Examiner*—Alana M Harris
(74) *Attorney, Agent, or Firm*—Pabst Patent Group LLP

(57) ABSTRACT

Labeled antibodies, antibody fragments or peptides binding to soluble cytokines or cytokine receptors are used to diagnose whether a patient has cancer or an autoimmune disease. In a preferred embodiment, a radiolabelled tag that is chemically bound to a peptide, antibody, or antibody fragment specific for sTNFR-1 and/or sTNFR2 is injected into a patient with a tumor, or suspected tumor, or with any disease associated with STNF-1/STNF-2. The patient is then imaged using standard nuclear imaging equipment to detect areas or sites of concentration of the radiolabel and/or receptor/inhibitor and/or antigen. By screening for cancer by the substances it produces, using an injected antibody to that substance with a tracer attached to it, one can detect cancer at a very early stage, potentially even microscopically.

11 Claims, No Drawings

OTHER PUBLICATIONS

Daugherty, et al., *Nucl. Acids Res.*, "Polymerase chain reaction facilitates the cloning, CDR-grafting, and rapid expression of a murine monoclonal antibody directed against the CD18 component of leukocyte integrins", 19:2471-2476 (1991).

Eliopoulos, et al., "The role of the CD40 pathway in the pathogenesis and treatment of cancer" *Curr Opin Pharmacol*, 4(4):360-7 (2004).

Engelmann, et al., "Two tumor necrosis factor-binding proteins purified from human urine. Evidence for immunological cross-reactivity with cell surface tumor necrosis factor receptors", *J Biol Chem*, 265(3):1531-6 (1990).

Feng, "Regulatory roles and molecular signaling of TNF family members in osteoclasts", *Gene*, 350(1):1-13 (2005).

Forrest, et al., "Modulation of cytokine release by purine receptors in patients with rheumatoid arthritis," *Clin Exp Rheumatol.*, 23(1):89-92 (2005).

Fraker, et al., "Protein and cell membrane iodinations with a sparingly soluble chloroamide, 1,3,4,6-tetrachloro-3a,6a-diphrenylglycoluril", *Biochem. Biophys. Res. Commun.*, 80:849-857 (1978).

Gadducci, et al., "Serum levels of soluble receptors for tumor necrosis factor (p55 and p75 sTNFr) in endometrial cancer", *Anticancer Res*, 16(5B):3125-8 (1996).

Gadducci, et al., "Serum levels of tumor necrosis factor (TNF), soluble receptors for TNF (55- and 75-kDa sTNFr), and soluble CD14 (sCD14) in epithelial ovarian cancer", *Gynecol Oncol*, 58(2):184-8 (1995).

Golovko, et al., "Vitamin D-induced up-regulation of tumour necrosis factor alpha (TNF-alpha) in prostate cancer cells", *Life Sci.*, 77(5):562-77 (2005).

Grell, et al., "The type 1 receptor (CD120a) is the high-affinity receptor for soluble tumor necrosis factor", *Proc Natl Acad Sci U S A.*, 95(2):570-5 (1998).

Grosen, et al., "Measurement of the soluble membrane receptors for tumor necrosis factor and lymphotoxin in the sera of patients with gynecologic malignancy", *Gynecol Oncol*, 50(1):68-77 (1993).

Hadziselimovic, "Reply: Urinary excretion of TNF receptors", *Gut*, 38(1):153-4 (1996), Abstract only.

Hasegawa, et al, "Increased soluble tumor necrosis factor receptor levels in the serum of elderly people", *Gerontology*, 46(4):185-8 (2000).

Holtmann, et al., "The emerging distinct role of TNF-receptor 2 (p80) signaling in chronic inflammatory disorders", *Arch Immunol Ther Exp (Warsz)*, 50(4):279-88 (2002).

Hyer, et al., "Synthetic triterpenoids cooperate with tumor necrosis factor-related apoptosis-inducing ligand to induce apoptosis of breast cancer cells", *Cancer Res*, 65(11):4799-808 (2005).

Iborra, et al., "Oxidative stress and autoimmune response in the infertile woman", *Chem Immunol Allergy*, 88:150-62 (2005).

Ireland, et al., "Interleukin (IL)-12 receptor beta1 or IL-12 receptor beta 2 deficiency in mice indicates that IL-12 and IL-23 are not essential for host recovery from viral encephalitis", *Viral Immunol.*, 18(2):397-402 (2005).

Jaakkola, "In vivo detection of vascular adhesion protein-1 in experimental inflammation", *Amer.J. Pathol.*, 157:463-471 (2000).

Jablonska, et al., "Tumor necrosis factor-alpha and soluble tumor necrosis factor receptors in the culture supernatants of polymorphonuclear cells and peripheral blood mononuclear cells from cancer patients", *Eur Cytokine Netw*, 9(2):155-9 (1998).

Jacob, et al., "Fiber-modified adenoviral vector expressing the tumor necrosis factor-related apoptosis-inducing ligand gene from the human telomerase reverse transcriptase promoter induces apoptosis in human hepatocellular carcinoma cells", *World J Gastroenterol*, 11(17):2552-6 (2005).

Jakobovits, "The long-awaited magic bullets: therapeutic human monoclonal antibodies from transgenic mice", *Exp. Opin. Invest. Drugs*, 7:607-614 (1998).

Kim, et al., "Identification of naturally secreted soluble form of TL1A, a TNF-like cytokine", *J Immunol Methods*, 298(1-2):1-8 (2005).

Lentz, "The phylogeny of oncology," *Mol Biotherm.*, 2:137-144 (1990).

Liu, et al., "Molecular mechanism of TNF signaling and beyond", *Cell Res*, 15(1):24-7 (2005).

Macallan, et al., "Development of a novel TNF alpha ligand-receptor binding assay for screening NATCHEM Libraries", *J Recept Signal Transduct Res*, 17(1-3):521-9 (1997).

Maier, et al., "Physiological levels of pro- and anti-inflammatory mediators in cerebrospinal fluid and plasma: a normative study", *J Neurotrauma*, 22(7):822-35 (2005).

Malmberg, "Effective immunotherapy against cancer: a question of overcoming immune suppression and immune escape?" *Cancer Immunol Immunother*, 53(10):879-92 (2004).

Mendez, et al., "Functional transplant of megabase human immunoglobulin loci recapitulates human antibody response in mice", *Nat. Genet.*, 15:146-156 (1997).

Mercer, et al., "Natural killer T cells: rapid responders controlling immunity and disease", *Int J Biochem Cell Biol.*, 37(7):1337-43 (2005).

Muc-Wierzgon, et al., "Circadian fluctuations of melatonin, tumor necrosis factor-alpha and its soluble receptors in the circulation of patients with advanced gastrointestinal cancer", *J Exp Clin Cancer Res*, 22(2):171-8 (2003).

Nagata, et al., "Cell membrane-specific epitopes on CD30: Potentially superior targets for immunotherapy", *Proc Natl Acad Sci U S A.*, 102(22):7946-51 (2005).

Nophar, et al., "Soluble forms of tumor necrosis factor receptors (TNF-Rs). The cDNA for the type I TNF-R, cloned using amino acid sequence data of its soluble form, encodes both the cell surface and a soluble form of the receptor", *EMBO J*, 9(10):3269-78 (1990).

Onsrud, et al., "Soluble tumor necrosis factor receptors and CA 125 in serum as markers for epithelial ovarian cancer", *Tumour Biol*, 17(2):90-6 (1996).

Onsrud, et al., "Comparison between soluble tumor necrosis factor receptors and CA125 in peritoneal fluids as a marker for epithelial ovarian cancer", *Gynecol Oncol*, 57(2):183-7 (1995).

Opala, et al., "Evaluation of soluble tumour necrosis factor alpha receptors p55 and p75 in ovarian cancer patients", *Eur J Gynaecol Oncol*, 26(1):43-6 (2005).

Penichet, et al, "Design and engineering human forms of monoclonal antibodies", *Drug Development Research*, 61:121-136 (2004).

Radcliff, et al., "Insulin-like growth factor-I regulates proliferation and osteoblastic differentiation of calcifying vascular cells via extracellular signal-regulated protein kinase and phosphatidylinositol 3-kinase pathways" *Circ Res.*, 96(4):398-400 (2005).

Reichert, "Monoclonal antibodies in the clinic", *Nature Biotechnology*, 19:819-822 (2001).

Ramacle-Bonnet, et al., "Membrane rafts segregate pro- from anti-apoptotic insulin-like growth factor-I receptor signaling in colon carcinoma cells stimulated by members of the tumor necrosis factor superfamily", *Am J Pathol*, 167(3):761-73 (2005).

Rzymski, et al., "Serum tumor necrosis factor alpha receptors p55/p75 ratio and ovarian cancer detection", *J Gynaecol Obstet*, 88(3):292-8 (2005).

Satoh, et al., "C-reactive protein co-expresses with tumor necrosis factor-alpha in the myocardium in human dilated cardiomyopathy", *Eur J Heart Fail*, 7(5):748-54 (2005).

Serwin et al., "[Soluble tumor-necrosis-factor-alpha receptor, type-1 as a marker of activity of psoriasis vulgaris and effects of its treatment]", *Przegl Lek*, 62(2):95-7 (2005), Abstract only in English.

Serwin, et al., "Soluble tumor necrosis factor alpha receptor type 1 in psolipsis patients treated with narrowband ultraviolet B" *Photodermatol Photoimmunol Photomed*, 21(4):210-1 (2005).

Shai, et al., "A prospective study of soluble tumor necrosis factor-alpha receptor II (sTNF-RII) and risk of coronary heart disease among women with type 2 diabetes", *Diabetes Care*, 28(6):1376-82 (2005).

Singh, et al., "C-reactive protein decreases tissue plasminogen activator activity in human aortic endothelial cells: evidence that C-reactive protein is a procoagulant", *Arterioscler Thromb Vasc Biol*, 25(10):2216-21 (2005).

Sukhikh, et al., "Disorders in cytokine gene expression in endometrial hyperplasia and effect of hormone therapy", *Bull Exp Biol Med.*, 139(2):235-7 (2005).

Takada, et al., "Indole-3-carbinol suppresses NF-kappaB and IkappaBalpha kinase activation, causing inhibition of expression of NF-kappaB-regulated antiapoptotic and metastatic gene products and enhancement of apoptosis in myeloid and leukemia cells", *Blood*, 106(2):641-9 (2005).

Tesarova, et al., "Soluble TNF and IL-2 receptors in patients with breast cancer", *Med Sci Monit*, 6(4):661-7 (2000).

Theiss, et al., "Tumor Necrosis Factor. (TNF) {alpha} Increases Collagen Accumulation and Proliferation in Intestinal Myofibroblasts via TNF Receptor 2", *J Biol Chem*, 280(43):36099-109 (2005).

Thomson, "Viruses and apoptosis," *Int J Exp Pathol*, 82(2):65-76 (2001).

Vaquero, et al., "Transient expression of a tumor-specific single-chain fragment and a chimeric antibody in tobacco leaves", *Proc Natl Acad Sci U S A.*, 96(20):11128-11133 (1999).

Vaughan, et al., "Human antibodies by design", *Nature Biotechnology*, 16:535-539 (1998).

Velders, et al., "New chimeric anti-pancarcinoma monoclonal antibody with superior cytotoxicity-mediating potency", *Cancer Res.*, 54:1753-1760 (1994).

Wajant, et al., "Tumor necrosis factor signaling", *Cell Death Differ*, 10(1):45-65 (2003).

Wozel, "[Etanercept An effective TNF alpha-antagonist in the treatment of psoriatic arthritis and chronic plaque psoriasis.]" *Hautarzt*, 56(9):819-830 (2005).

Zeromski, "Significance of tumor-cell receptors in human cancer", *Arch Immunol Ther Exp (Warsz)*, 50(2):105-10 (2002).

Adolf and Frühbeis, "Monoclonal antibodies to soluble human TNF receptor (TNF binding protein) enhance its ability to block TNF toxicity.", *Cytokine*, 4(3):180-184 (1992).

Riechmann, et al., "Reshaping human antibodies for therapy.", *Nature*, 332(6162):323-327 (1988).

\* cited by examiner

METHODS FOR DIAGNOSIS USING ANTI-CYTOKINE RECEPTOR ANTIBODIES

BACKGROUND OF THE INVENTION

This application claims priority to U.S. Ser. No. 60/590,400 filed Jul. 22, 2004.

The present invention is generally in the field of diagnosing areas in the body that contain antigenic, diseased, transformed or neoplastic tissue that is associated with an inflammatory response. This is accomplished by the administration and imaging of radiolabelled antibodies to tumor necrosis factor receptor. This diagnostic test is intended for early diagnosis of disease in mammals.

The two main causes of death in this country are heart disease and cancer. Researchers today are finding more and more evidence that these diseases start with an inflammatory response involving the immune system. The various response organs, such as the gut, skin, lungs, bone marrow, thymus, and spleen, react with the production of special messenger substances that activate/create macrophages, T-cells, B-cells and NK-cells, all with specific functions to protect the body from invasion of other living organisms as well as toxins. Some of these messenger substances include cytokines such as TNF and C-reactive protein, lymphotoxins, and leukotrienes.

Tumor Necrosis Factor (TNF) is a pirotrophic pro-inflammatory cytokine produced by macrophages. The amount of TNF is crucial; too much can cause cachexia and septic shock, while too little can allow infection and cancer. The body's white cells will recognize a cancer cell, bind to it (if not blocked/inhibited) and kill it with TNF. This reaction is inhibited by immunosuppressants, either from outside the body (medications, radiation, environmental toxins) or from within (tumor production of cell surface TNF receptors (sTNF-R1 and sTNF-R2). If the inhibitors/blockers of the normal white cell response can be removed, then the immune system can attack and kill the affected cells.

The TNF receptors (sTNF-R1 and sTNF-R2) are present on all mammalian cells. Over production and shedding of these receptors into body fluids causal to acquired immune tolerance. These soluble shed receptors are found in increased quantities in the immediate cellular microenvironment of antigenic tissues and cells. (Lentz M R. The phylogeny of oncology. *Mol Biotherm.* 2:137-144 (1990)). The result of this over-production and shedding is to protect the antigenic cell or an antigen from an otherwise normal inflammatory/immune response.

The most crucial aspect in the successful treatment of any cancer is early detection. Likewise, it is crucial to properly diagnose chronic and acute inflammatory conditions, i.e, autoimmune diseases, before tissue and organ destruction occurs. PET, MRI, and CT scans are limited in their sensitivity.

It is therefore an object of the present invention to provide a method and system for early detection of tumors and other types of diseased tissue.

SUMMARY OF THE INVENTION

Labeled antibodies, antibody fragments or peptides binding to soluble cytokines or cytokine receptors are used to diagnose whether a patient has cancer or an autoimmune disease. In a preferred embodiment, a radiolabelled tag that is chemically bound to a peptide, antibody, or antibody fragment specific for sTNFR-1 and/or sTNFR2 is injected into a patient with a tumor, or suspected tumor, or with any disease associated with STNF-1/STNF-2. The patient is then imaged using standard nuclear imaging equipment to detect areas or sites of concentration of the radiolabel and/or receptor/inhibitor and/or antigen. By screening for cancer by the substances it produces, using an injected antibody to that substance with a tracer attached to it, one can detect cancer at a very early stage, potentially even microscopically.

DETAILED DESCRIPTION OF THE INVENTION

I. Compositions

Antibodies

The composition for administration to a patient for early detection of cancer consists of antibodies, or antibody fragments, to cytokines or cytokine receptors. In the preferred embodiment, the antibodies will typically be reactive with both the soluble and immobilized forms of the receptor. These include soluble tumor necrosis factor receptor ("sTNF-R"), either sTNFI or sTNR2, soluble interleukin-2 receptor ("sIL-2R"), soluble interleukin-1 receptor ("sIL-1R"), soluble interleukin-6 receptor ("sIL-6R"), soluble interleukin-12 (IL-12R) or soluble interferon-gamma receptor ("sIFN-gammaR"). These materials are all commercially available and described in detail in the literature.

As used herein, "antibody" refers to antibody, antibody fragments or binding peptides (single chain, recombinant, or humanized), that are immunoreactive with the receptor molecules. In the most preferred embodiment, the antibody is reactive with the carboxy-terminus of the shed receptor molecules, thereby avoiding concerns with signal transduction by the receptor that is still present on the cell surface.

Antibodies can be obtained from various commercial sources such as Genzyme Pharmaceuticals. Alternatively, antibodies to the receptor proteins can be generated by standard techniques, typically immunization using human receptor proteins. Antibodies are typically generated by immunization of an animal using an adjuvant such as Freund's adjuvant in combination with an immunogenic amount of the protein administered over a period of weeks in two to three week intervals, then isolated from the serum, or from hybridomas made from immunoglobulin producing cells from the immunized animals, which express the antibodies in culture.

Because the methods for immunizing animals yield antibody which is not of human origin, the antibodies could elicit an adverse effect if administered to humans. Methods for "humanizing" antibodies, or generating less immunogenic fragments of non-human antibodies, are well known. A humanized antibody is one in which only the antigen-recognized sites, or complementarily-determining hypervariable regions (CDRs) are of non-human origin, whereas all framework regions (FR) of variable domains are products of human genes. These "humanized" antibodies have less potential for a xenographic rejection stimulus when introduced to a human recipient. Humanized antibodies are defined as a monoclonal antibody ("mAb") constructed with only the antigen-binding regions (also called complementary-determining regions or CDRs) derived from a mouse, and the remainder of the variable regions, and constant regions, derived from a human source (Reichert *Nature Biotechnology* 19: 819-822 (2004)). The procedure for constructing humanized antibodies is as follows. A mouse hybridoma cell line expressing the desired antibody is grown in an appropriate culture medium. Cells are harvested and total RNA is isolated. Complementary DNA (cDNA) is generated that codes for the variable domains of the mouse antibody to be humanized. This is accomplished using polymerase chain reaction (PCR) primers that hybridize to the 5' ends of the mouse leader sequences and to the 5' ends of the mouse constant regions. The light chain and heavy chain variable regions are cloned. PCR amplification of the cDNA is accomplished using light and heavy chain specific primers. The PCR product is cloned directly into a vector. This vector is transformed into bacteria. The bacteria are selected for colonies containing the vector with the mouse variable regions.

Construction of the humanized antibody involves modifying the mouse variable regions at the 5' and 3' ends using PCR primers to create restriction enzyme sites for convenient insertion into expression vectors, and to incorporate splice-donor sites for RNA splicing of the variable and constant regions. The modified mouse variable regions are then inserted into the framework regions of a human antibody. The final vector encodes the CDRs "grafted" or "humanized" into the framework regions of the human variable region and the human constant region (Penichet et al. *Drug Development Research* 61: 121-136 (2004)). These vectors often contain human cytomegalovirus (CMV) enhancer and promoter for transcription, a gene for selection of transformed cells (often neomycin), and the simian virus 40 origin of replication for COS cells. Preliminary expression and analysis of the humanized antibody is accomplished by transfection of mammalian cells. The concentration of the antibody produced can be analyzed by using enzyme-linked immunosorbent assay (ELISA). The binding activity of the antibody can be determined by competitive ELISA and/or equilibrium dialysis.

Antibodies humanized this way have been shown to have up to one-third greater binding affinity than the corresponding murine antibody (Adair *Immunol. Rev.* 130: 5-40 (1992). Allergenicity is also reduced with humanized antibodies. It has been demonstrated that 20-40% of patient exhibit HAMA reactions to murine antibodies, while only 7% have a HAMA reaction to humanized antibodies (Vaughan et al. *Nature Biotechnology* 16: 535-539 (1998); Maloney In: Monoclonal antibody-based therapy of cancer. New York: Marcel Dekker p. 53-79 (1998); Berkower *Curr. Opin. Biotechnology* 7: 622 (1996); Brumley et al. *AORN J.* 62: 343-355 (1995); Esteva et al In: Monoclonal antibody-based therapy of cancer. New York: Marcel Dekker p. 309-338 (1998). See also Daugherty, et al., *Nucl. Acids Res.,* 19:2471-2476 (1991); Clackson, T., et al., Nature, 352:624-688 (1991); and Kabat, H. A., et al., Sequences of Proteins of Immunological Interest, 4$^{th}$ Ed. (U.S. Dept. Health and Human Services, Bethesda, Md., 1987). Methods to make chimeric monoclonal antibodies by DNA recombinant technology, as described by Velders, et al. Cancer Res., 54: 1753-1760 (1994), are also described in Vaquero, Appl. Biol. Sci. 96: 20, 11128-11133 (1999, and Jaakkola, Amer. J. Pathol. 157:463-471 (2000).

Alternatively, the immunogenic stimulus presented by the monoclonal antibodies may be decreased by the use of Pharmacia's (Pharmacia LKB Biotechnology, Sweden) "Recombinant Phage Antibody System" (RPAS), which generates a single-chain Fv fragment (ScFv) which incorporates the complete antigen-binding domain of the antibody. In the RPAS, antibody variable heavy and light chain genes are separately amplified from the hybridoma mRNA and cloned into an expression vector. The heavy and light chain domains are co-expressed on the same polypeptide chain after joining with a short linker DNA which codes for a flexible peptide. This assembly generates a single-chain Fv fragment (ScFv) which incorporates the complete antigen-binding domain of the antibody. Compared to the intact monoclonal antibody, the recombinant ScFv includes a considerably lower number of epitopes, and thereby presents a much weaker immunogenic stimulus when injected into humans.

Human antibody-producing XenoMouse strains can be used to generate potent fully human anti-TNFR monoclonal antibodies. These mouse strains are engineered to be deficient in mouse antibody production and to contain integrated megabase-sized fragments from the human heavy and κlight chain loci with the majority of the human antibody gene repertoire. The human immunoglobulin loci provide the XenoMouse strains with the ability to produce high-affinity human MAbs to a broad spectrum of antigens including human antigens, as described by Mendez, et al., Nat. Genet., 15: 146-156 (1997). See also Jakobovits, Exp. Opin. Invest. Drugs, 7: 607-614 (1998).

Antibodies (monoclonal, chimeric and chimeric-mutated, or single-chain antibody (scAb) can be purified from ascitic fluid by affinity chromatography. They are precipitated from ascite (Amersham Pharmacia Biotech) by ammonium sulfate and purified on protein-A Sepharose™. IgG is eluted with citrate buffer, pH 3.5, neutralized, and loaded onto an HSA-Sepharose™ column, which separates the chimeric antibodies (HSA-specific) from mouse host IgGs. F(ab')$_2$ fragments are obtained by pepsin digestion of the corresponding IgG in acetate buffer, pH 4.6, followed by chromatography on a Superdex™ 75 column (fast protein liquid chromatography) and affinity chromatography on protein A-Sepharose™. Purity of antibodies and F(ab')$_2$ fragments is verified by SDS-PAGE under reduced and non-reduced conditions and visualized by staining with Coomassie Blue R-250 (Sigma).

Radiolabels

The humanized antibody is labeled with a detectable substance. The tracer can be anything that can be detected by conventional nuclear medicine scanning devices such as $^{131}$I or $^{125}$I. $^{125}$I is mostly used for immunochemical analyses due to its low-energy gamma and X-ray radiation for easier detection. Iodination of antibodies or other proteins is a straightforward and effective method of labeling. This tracer is attached to the Fc tail end of the antibody so that it will not interfere with the subsequent in vivo antigen (R1/R2) to antibody response.

For example, monoclonal antibodies can be radiolabeled according to the iodogen method of Fraker, et al., Biochem. Biophys. Res. Commun., 80: 849-857 (1978). Briefly, 1.0 ml of antibody (5 mg/ml) and 100 μl 0.5 M sodium phosphate (pH 7.2) are added to a iodogen-coated tube (50 μg). Subsequently, 200 μCi of Na$^{125}$I (Amersham-Cygne, Hertogenbosch, The Netherlands) or 8 mCi of Na$^{131}$I (Nordion, Fleurus, Belgium) are added. After 15 min of incubation at room temperature, the reaction mixture is applied on a PD-10 column (Pharmacia, Woerden, The Netherlands) and eluted with a phosphate buffered NaCl solution (pH 7.4; 8.2 g/liter NaCl, 1.9 g/liter Na$_2$HPO$_4$.2H$_2$O, and 0.3 g/liter NaH$_2$PO$_4$.2H$_2$O). The first activity peak eluted from the PD-10 column is collected, and cold antibody added to obtain a monoclonal antibody solution with a specific activity of 10 μCi $^{125}$I/mg monoclonal antibody or a specific activity of 0.7 mCi $^{131}$I/mg monoclonal antibody. ITLC is used to determine the presence of free radioiodine using Gelman ITLC-SG strips (Gelman Sciences, Inc., Ann Arbor, Mich.) and 0.15 M sodium citrate (pH 5.5) as the mobile phase (release criterion: <5% free radioiodine).

The antibodies can also be labeled with I$^{123}$ and I$^{131}$, respectively, using the standard chloramine-T method. Briefly, an adequate amount of I$^{123}$ or I$^{131}$ in 100 to 150 μl of 0.18 mol/L phosphate buffer at pH 7.5 and 100 μg of antibody were mixed with 0.15 μg chloramine-T. After 5 minutes, the radiolabeled antibody was purified using PD-10 Sephadex™ G-25 size exclusion column (Pharmacia Biotech, Uppsala, Sweden) with 2% albumin/0.9% sodium chloride mobile phase. The purity of the radiolabeled immunoconjugate is determined by instant thin layer chromatography with 20% trichloro acetic acid as a solvent.

Carriers for Administration to Patients

The antibodies can be formulated in standard pharmaceutical carriers for administration to patients in need thereof. These include saline, phosphate buffered saline, and other aqueous carriers, and liposomes, polymeric microspheres and other controlled release deliver devices, as are well known in the art. The antibodies can also be administered with adjuvant, such as muramyl dipeptide or other materials approved for use in humans (Freund's adjuvant can be used for administration of antibody to animals).

II. Method of Administration and Detection

The antibody is administered to a patient in need thereof in an effective amount to bind to the tumors or areas of inflammation. For example, on day 0, patients received a first i.v. infusion of 5 mg of monoclonal antibody tracer labeled with 50 μCi of $^{125}$I. Later, a second i.v. infusion of 5 mg of monoclonal antibody tracer labeled with 3.5 mCi of $^{131}$I is administered. Whole-body images are recorded 1 h, 2 days, and 4 days after the second infusion, using a dual-headed gamma camera equipped with a high-energy collimator (Multispect 2; Siemens Inc., Hoffman Estates, Ill.)

In the most preferred embodiment, unlabelled antibody is administered first to bind to "background" soluble receptor and increase the contrast with bound antibody. Alternatively, the antibody is first injected without a tracer to absorb the soluble R1/R2 (normal levels known to be 750-1750 pcg/mL for R1 and 1500-3100 pcg/mL for R2), then another dose of the antibody injected with the tracer for a cleaner scan and to assure attraction to the R1/R2 cloud around the cancer. For the imaging experiments a nonbinding human chimeric antibody can also be used as a negative control.

In the preferred embodiment, the scan is similar to a bone scan, although PET or other methods of detection could also be used. Nuclear imaging uses low, relatively non-toxic doses of radioactive substances that are linked to compounds used by the body's cells or compounds that recognize tumor cells. Using special detection equipment, the radioactive substances can be traced in the body to see where and when they concentrate. In a preferred embodiment, the device is a Magnetic Resonance Imaging (MRI) device that is equipped with a "zoom" lens and a magnetic tracer such that a definitive pattern will be observed allowing differentiation between areas of cancer and inflammation or infection. Two main areas of nuclear imaging are radiolabeled antibodies and PET scans. A SPECT (single photon emission computed tomography) transmission scan can be done to detect the radioactive substance and reveal where the tumor is located. Using radiolabeled monoclonal antibodies in this way is sometimes called immunoscintigraphy.

It is preferable to have data from administration of the antibodies to normal subjects to determine any "background noise" since there is soluble R1/R2 in the blood without the presence of cancer. The amount of noise also depends on age and renal function of the individual (greater clearance in younger patients, so a lower threshold of R1/R2 values would be used). Removing this "noise" increases the sensitivity of the test. In addition, scanning with the antibody in all stages of cancer will provide more accurate information for staging and to prove the validity/efficacy of this testing technique.

All of the costs with scanning are less than $1000/person. This testing will help diagnose and locate the cancer in its infancy. Routine optimization can be used to increase imaging of the patient, and determining how long to wait before the scan is performed to allow the best antigen-antibody response to occur; alternatively one can also scan at set intervals from maximum flush to complete washout). Standard care is used to address any potential anaphylactoid or anaphylactic reaction to the tracer and/or antibody (risk reduced by identifying those at risk through skin testing), and knowing the amount of antibody to inject to elicit a measurable response radiologically, but not cause enough of an immune response to result in patient distress.

In addition to detection of tumors, the compositions can be used to detect areas of any tissue inflammation releasing pro-inflammatory cytokines and chemokines as well as specific anti-cytokines and chemokines. By locating the anatomical site of this process early in the natural history of the disease, one can intervene early and stop or inhibit the disease process before it becomes clinically manifest. For example, one of these substances, C-reactive protein, is known to be a very sensitive risk indicator to stroke and heart disease. Unfortunately, C-reactive protein is a pentameric protein made by the liver in response to dead or dying tissue, which release cationic protein. By the time this molecule is elevated in blood, tissue is already dead and dying. By tagging cytokine and anti-cytokine antibodies and tracer, areas of disease in the earliest stages can be identified and treated before tissues die. Atherosclerotic plaque is thought to be deposited in an artery in response to tissue invasion of cytomegalovirus ("CMV"), *C. pneumoniae*, or *H. pylori*. An antigen-antibody ("Ag-Ab") test for these organisms or for the localization of the consequent inflammatory response, should also allow early definitive treatment and provide for subsequent follow-up testing to identify any association with an infective agent and evaluate the adequacy of therapy for prognosis of the disease. This type of testing can be used to test for other autoimmune diseases, including rheumatoid arthritis (RA), multiple sclerosis (MS), and systemic lupus erythematosus (SLE).

The present invention will be further understood with reference to the following non-limiting examples.

EXAMPLE 1

Measurement of sTNFR-1 and sTNFR-2 Levels Allow Early Diagnosis of Cancer

A patient in her 50's was diagnosed with Hashimoto's Thyroiditis. Hashimoto's Thyroiditis is a type of autoimmune thyroid disease in which the immune system attacks and destroys the thyroid gland. The thyroid helps set the rate of metabolism—the rate at which the body uses energy. Hashimoto's prevents the gland from producing enough thyroid hormones for the body to work correctly. Common symptoms of Hashimoto's Thyroiditis are fatigue, depression, sensitivity to cold, weight gain, muscle weakness, coarsening of the skin, dry or brittle hair, constipation, muscle cramps, increased menstrual flow, and goiter. Several years later the patient was diagnosed with Type I Diabetes Mellitus (Type I DM). Type 1 DM is considered to be a T-lymphocyte-dependent autoimmune disease characterized by infiltration and destruction of the islets of Langerhans, the endocrine unit of the pancreas. Symptoms of type 1 diabetes are often polyuria (frequent urination) and polydipsia (increased thirst and consequent increased fluid intake). There may also be weight loss (despite normal or increased eating), increased appetite, and irreducible fatigue. Another common presenting symptom is altered vision. Especially dangerous symptoms in diabetics include the smell of acetone on the patient's breath (a sign of ketoacidosis), Kussmaul breathing (a rapid, deep breathing), and any altered state of consciousness or arousal (hostility and mania are both possible, as is confusion and lethargy). Type I DM can lead to diabetic coma, which causes unconsciousness, early symptoms include polyuria, nausea, vomiting and abdominal pain, with lethargy and somnolence a later development, progressing to unconsciousness and death if untreated. Unlike other Type I DM patients undergoing insulin therapy, the blood glucose levels of the patient described herein were extremely difficult to manage. The patient's glucose levels ranged from 500 mmol/L to 28 mmol/L within a 15 minute span and could not be controlled. The observed fluctuation in glucose levels and the difficulty in managing these glucose levels are very unusual. The patient was fitted with an insulin pump, but this did not resolve the problem. The patient was then analyzed for levels of C-Reactive Protein (CRP) and erythrocyte sedimentation rate (ESR). The CRP test is a test which measures the concentration in blood serum of a special type of protein produced in the liver that is present during episodes of acute inflammation or infection. High levels of CRP may be an indicator of several conditions, including rheumatoid arthritis, rheumatic fever, cancer, tuberculosis, pneumonia, heart attack, and lupus. The erythrocyte sedimentation rate (ESR) is another test which gives information about non-specific inflammation. The ESR test involves placing a blood sample in a tube and determining how fast the red blood cells settle to the bottom in one hour. The patient had normal levels of CRP and ESR. Despite the normal levels of CRP and ESR, the patient was still experiencing fluctuations in glucose levels. A cancer cell has 6 times more insulin receptors and 10 times more Growth Hormone (GH) receptors than a normal cell. Therefore, a cancer cell will take up more insulin and more GH than a normal cell. This is why cancer cells grow at the expense of the host's body. This would also explain the patient's uncontrollable fluctuation in glucose levels. Therefore, the patient was then analyzed by the method described above for sTNFR-1 and sTNFR-2 levels in order to determine if the patient had cancer. Levels of TNF-alpha were high. Levels of TNF-alpha receptor I and II were also high. The high levels of sTNFR-1 and sTNFR-2 suggested that the patient had cancer. However, the patient's PET scan was normal. By analysis of sTNFR-1 and sTNFR-2 levels, the patient was diagnosed with cancer. The patient had vulvar sclerosis (VS) with increased p53 expression. Keratinocytes affected by VS show a proliferative phenotype and can exhibit markers of neoplastic progression such as increased p53 expression and DNA aneuploidy. As a chronic scarring inflammatory dermatosis, VS could act as both "initiator and promoter" of carcinogenesis. Because keratinocytes of VS significantly express tumor suppressor gene p53 protein, the p53 gene may be involved early in this proposed pathway of carcinogenesis. Prior to analysis of the sTNFR-1 and sTNFR-2 levels the patient was not being treated for cancer. The VS had been diagnosed "precancerous" and controlled and therefore, was not being treated. The patient is now being treated for cancer. These results demonstrate that the methods described herein for early detection of tumors and other types of diseased tissue are sensitive and efficacious.

EXAMPLE 2 sTNFR-1 and sTNFR-2 is a Highly Sensitive Test for Cancer

A 62 year old patient was found to have a posterior uterine mass that had developed sometime over a period of 3 years. The patient was diagnosed with cancer and was told that it would be necessary to have exploratory laparoscopic surgery and to remove everything that looked like potential cancer for biopsy. Cancer can be diagnosed by taking a sample of the tumor (biopsy). During a biopsy, the tumor material is examined by a pathologist, a physician who specializes in diagnosing diseases by looking at the cells under a microscope. Laparoscopy is the usual first step in confirming the presence of a mass and obtaining a tissue sample for biopsy. Laparoscopic surgery uses small incisions and specially designed instruments to enter the abdomen or pelvis. In exploratory laparoscopy, a larger incision is made in the skin and abdominal muscles to gain access to the pelvic region. Exploratory laparoscopy is a thorough attempt to find the exact extent of cancer spread. To identify possible invasion by the cancer, samples are taken of structures in the pelvis and abdomen including the diaphragm (the muscle that separates the organs of the chest from the organs of the abdomen), the peritoneum (the membrane that lines the abdomen), the omentum (a fatty membrane that covers the organs of the abdomen), lymph nodes, bladder, and bowel. The goal is to remove as much cancerous tissue as possible (debulking). This may involve removing one or both ovaries (oophorectomy), the uterus (hysterectomy), fallopian tubes (salpingectomy), and other organs. Typically, the surgeon does not know ahead of time exactly which organs and structures will require removal. Therefore, it is recommended that the full extent of the operation be discussed with a surgeon before consenting to the procedure. The procedure carries a slight risk of puncturing a blood vessel or organ, which could cause blood to seep into the abdominal cavity. Puncturing the intestines could allow intestinal contents to seep into the cavity. These are serious complications and major surgery may be required to correct the problem. There is also the possibility that it may become apparent that open surgery is required. Rare complications include hemorrhage, inflammation of the abdominal cavity lining, abscess, and problems related to general anesthesia. Therefore, less invasive methods than surgery as tools for diagnosing cancer would be useful to prevent unnecessary surgeries.

In this case, the patient did not undergo surgery and obtained a second opinion. The patient was analyzed as described by the method above for sTNFR-1 and sTNFR-2 levels in order to determine if the patient had cancer. Both sTNFR-1 and sTNFR-2 levels were in the normal range. These results indicate that the uterine mass was benign and that the patient did not have cancer. The patient was examined by a third physician who indicated that the patient did not cancer. The patient elected to wait for three months and undergo a repeat PET scan. The patient did not have cancer and therefore, a painful surgery procedure was avoided. These results demonstrate that the methods described herein for detection of tumors and other types of diseased tissue are sensitive, efficacious, and a viable alternative to exploratory surgery.

We claim:

1. A method for diagnosing inflammation or cancer comprising administering to a patient, effective amount of antibody or antibody fragments binding to soluble tumor necrosis factor receptor 1 ("TNFR1") or tumor necrosis factor 2 ("TNFR2"), to bind the circulating soluble receptor, then
    administering an effective amount of a labeled antibody binding to the tumor necrosis factor receptor to bind the tumor necrosis factor receptor on the surface of tumor cells and in the tumor microenvironment, and
    imaging the patient to detect labeled antibody bound to the tumor necrosis factor receptor on the surface of the tumor cells and in the tumor microenvironment.

2. The method of claim 1 wherein the antibodies are humanized monoclonal antibodies.

3. The method of claim 1 wherein the antibodies are labeled with a label selected from the group consisting of $I^{125}$, $I^{123}$ and $I^{131}$.

4. The method of claim 1 wherein the patient has cancer.

5. The method of claim 1 wherein the patient has an autoimmune disease.

6. The method of claim 1 wherein the patient has a chronic or acute infectious disease.

7. The method of claim 1 wherein 5 mg of radiolabeled antibody is intravenously administered on day zero, then a second infusion of 5 mg of labeled antibody is administered, and whole-body images recorded one hour, 2 days, and 4 days after the second infusion.

8. The method of claim 1 wherein the patient is imaged one, two or four days after administration of labeled antibody.

9. The method of claim 1 wherein the labeled antibody is detected using PET.

10. The method of claim 1 wherein the labeled antibody is detected using MRI.

11. The method of claim 1 wherein the antibodies further include antibodies selected from the group consisting of soluble interleukin-1 receptor ("sIL-1R"), soluble interleukin-6 receptor ("sIL-6R"), soluble interferon-gamma receptor ("sIFN-gammaR"), and soluble interleukin-12 receptor (sIL-12R).

* * * * *

UNITED STATES PATENT AND TRADEMARK OFFICE
CERTIFICATE OF CORRECTION

PATENT NO.        : 7,727,528 B2
APPLICATION NO.   : 11/185335
DATED             : June 1, 2010
INVENTOR(S)       : Deborah Kay Adcock Page 1 of 1

It is certified that error appears in the above-identified patent and that said Letters Patent is hereby corrected as shown below:

Claim 1, column 8, line 57, replace "patient, effective" with --patient, an effective--.

Signed and Sealed this
Twenty-seventh Day of September, 2011

David J. Kappos
*Director of the United States Patent and Trademark Office*